United States Patent
Anderson et al.

(10) Patent No.: US 7,682,316 B2
(45) Date of Patent: Mar. 23, 2010

(54) IMPLANTABLE HEART SOUND SENSOR WITH NOISE CANCELLATION

(75) Inventors: David A. Anderson, Andover, MN (US); Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 196 days.

(21) Appl. No.: 11/781,734

(22) Filed: Jul. 23, 2007

(65) Prior Publication Data

US 2009/0030334 A1 Jan. 29, 2009

(51) Int. Cl.
*A61B 5/02* (2006.01)
(52) U.S. Cl. .................. 600/528; 128/715; 600/514; 607/5
(58) Field of Classification Search .............. 600/27, 600/28, 508, 514, 522, 523, 527, 528; 607/18, 607/36, 38, 60, 62
See application file for complete search history.

(56) References Cited

U.S. PATENT DOCUMENTS

| | | | |
|---|---|---|---|
| 4,180,078 A | 12/1979 | Anderson | |
| 4,438,772 A | 3/1984 | Slavin | |
| 4,672,977 A | 6/1987 | Kroll | |
| 5,163,427 A | 11/1992 | Keimel | |
| 5,188,105 A | 2/1993 | Keimel | |
| 5,372,139 A | 12/1994 | Holls et al. | |
| 5,470,345 A | 11/1995 | Hassler et al. | |
| 5,554,177 A | 9/1996 | Kieval et al. | |
| 5,683,432 A | 11/1997 | Goedeke et al. | |
| 6,236,882 B1 | 5/2001 | Lee et al. | |
| 6,478,744 B2 | 11/2002 | Mohler | |
| 6,527,729 B1* | 3/2003 | Turcott | 600/528 |
| 6,869,404 B2 | 3/2005 | Schulhauser et al. | |
| 7,035,684 B2 | 4/2006 | Lee et al. | |
| 7,424,321 B2* | 9/2008 | Wariar et al. | 600/514 |
| 2004/0230243 A1 | 11/2004 | Haefner | |
| 2005/0043763 A1 | 2/2005 | Marcovechhio et al. | |
| 2007/0049975 A1* | 3/2007 | Cates et al. | 607/5 |
| 2007/0049977 A1 | 3/2007 | Von Arx | |
| 2007/0156190 A1 | 7/2007 | Cinbis | |

OTHER PUBLICATIONS

Widrow, Bernard et al. "Adaptive Noise Cancelling: Principles and Applications" Proceedings of the IEEE, Dec. 1975, pp. 1692-1716, Vol. 63.
International Search Report, PCT/US2008/070105, Mar. 11, 2008, 9 Pages.

* cited by examiner

*Primary Examiner*—Mark W Bockelman
*Assistant Examiner*—Elizabeth K So
(74) *Attorney, Agent, or Firm*—Stephen W. Bauer; Michael C. Soldner (57) ABSTRACT

An implantable medical device system senses a first signal using a first acoustical sensor adapted to be operatively positioned in a first internal body location for sensing heart sounds in a patient. The system includes a second acoustical sensor adapted to be operatively positioned in a second internal body location for sensing sounds in the patient and generate a second signal that is less responsive to the heart sounds than the first acoustical signal. An implantable medical device including a housing and a processor enclosed in the housing receives the first signal and the second signal and generates a corrected first signal by canceling non-cardiac signals in the first signal using the second signal.

9 Claims, 6 Drawing Sheets

IMPLANTABLE HEART SOUND SENSOR WITH NOISE CANCELLATION

FIELD OF THE INVENTION

The present invention generally relates to an implantable medical device system, and more particularly, to an implantable medical device system including an acoustical sensor for sensing heart sounds.

BACKGROUND

The detection of heart sounds using an acoustical sensor has been proposed for use in implantable medical device systems for use in detecting heart rhythms, verifying cardiac capture subsequent to a pacing pulse, and evaluating cardiac hemodynamics. Different and unique sounds are emitted from the heart during various points in the cardiac cycle which can be evaluated to monitor the heart rhythm as well as derive metrics of heart function. An acoustical sensor may be incorporated in an implantable medical device (IMD), such as a pacemaker, implantable cardioverter defibrillator (ICD) or implantable cardiac monitor, or carried by a medical lead extending from the IMD. One limitation in utilizing implantable acoustical sensors for evaluating heart sounds is the non-cardiac noise that is also sensed by the acoustical sensor and interferes with the detection and processing of heart sounds. Such non-cardiac noise can arise from both physiologic noise sources such as respiration, gastrointestinal, voice, coughing, muscle movement and the like, and non-physiologic noise sources present outside the patient's body.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
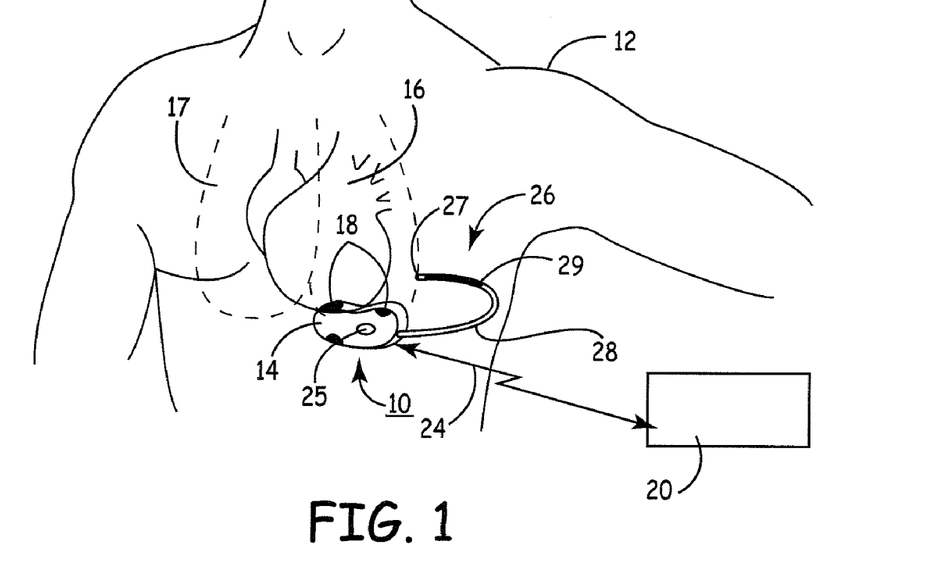
FIG. 1 shows subcutaneous ICD (SubQ ICD) implanted in patient.

FIG. 1 is a schematic diagram of a subcutaneous ICD (SubQ ICD) 10 implanted in patient 12. SubQ ICD 10 includes a housing 14. Housing 14 is generally shaped to promote ease of subcutaneous implant and minimize patient discomfort and is shown to be generally ovoid though embodiments of the invention are not limited to a particular housing geometry. SubQ ICD 10 is adapted to be implanted outside the ribcage of patient 12, anterior to the cardiac notch.

A first acoustical sensor 25 is shown mounted along the housing 14 of SubQ ICD 10. SubQ ICD 10 further includes a sensing electrode array 18 including three electrodes mounted on housing 14 for use in sensing subcutaneous ECG signals. It is recognized that in various embodiments of the invention, one or more electrodes, or no electrodes at all, may be incorporated on the SubQ ICD housing 14.

A subcutaneous sensing and cardioversion/defibrillation therapy delivery lead 28 is electrically coupled to SubQ ICD 10 via a connector block (not shown). Lead 28 includes a high voltage coil electrode 29 and may include one or more sensing electrodes (not shown) for use in sensing subcutaneous ECG signals. Lead 28 is tunneled subcutaneously to a posterior location adjacent a portion of a latissimus dorsi muscle of patient 12. Specifically, lead 28 is tunneled subcutaneously from the median implant pocket of SubQ ICD 10 laterally and posteriorly to the patient's back to a location opposite the heart such that the heart 16 and lungs 17 are disposed between the SubQ ICD 10 and the distal end 26 of lead 28. A second acoustical sensor 27 is shown positioned near the distal end 26 of lead 28 such that the lungs 17 are between the sensor 27 and the patient's heart 16.

The first acoustical sensor 25 is positioned in operative relation to the heart such that signals generated by sensor 25 will include heart sounds with additional signal contributions arising from physiological sources, such as muscle movement, respiration, gastrointestinal noise, voice, or the like as well as any non-physiological noise sources present external to the patient. The second acoustical sensor 27 is positioned at an internal body location such that signals generated by sensor 27 will be less responsive to heart sounds, i.e. lower heart sound amplitudes, than the first acoustical sensor 25, but will include non-cardiac noise signals. In particular, the patient's lungs 17 will act to filter cardiac sounds from the signal generated by sensor 27. The signal generated by sensor 27 will include other physiological and non-physiological noise and can therefore be used in noise cancellation schemes for removing or at least suppressing such noise signals from the signal generated by the first acoustical sensor 25.

The acoustical sensors 25 and 27 may be implemented as microphones 1-, 2-, or 3-axis accelerometer devices, which may be capacitive, thermal, piezoelectric or piezoresistive sensors. Implantable acoustical sensors for heart sound monitoring are generally disclosed in U.S. Pat. No. 6,869,404 (Schulhauser, et al.), in U.S. Pat. No. 5,554,177 (Kieval et al.), and U.S. Pat. No. 7,035,684 (Lee et al.), all of which patents are hereby incorporated herein by reference in their entirety. The first acoustical sensor 25 may be bonded to the external or internal surface of the housing 14 and electrically coupled to circuitry contained within the SubQ ICD housing via any necessary conductors and feedthroughs. Alternatively, sensor 25 may be attached to a hybrid circuit located inside the housing 14.

Further referring to FIG. 1, an external device 20, which may be embodied as a home monitor or programmer is shown in telemetric communication with SubQ ICD 10 by communication link 24, which may be an RF link established via Bluetooth, WiFi, MICS, or as described in U.S. Pat. No. 5,683,432 "Adaptive Performance-Optimizing Communication System for Communicating with an Implantable Medical Device" to Goedeke, et al and incorporated herein by reference in its entirety.

Figure 2:
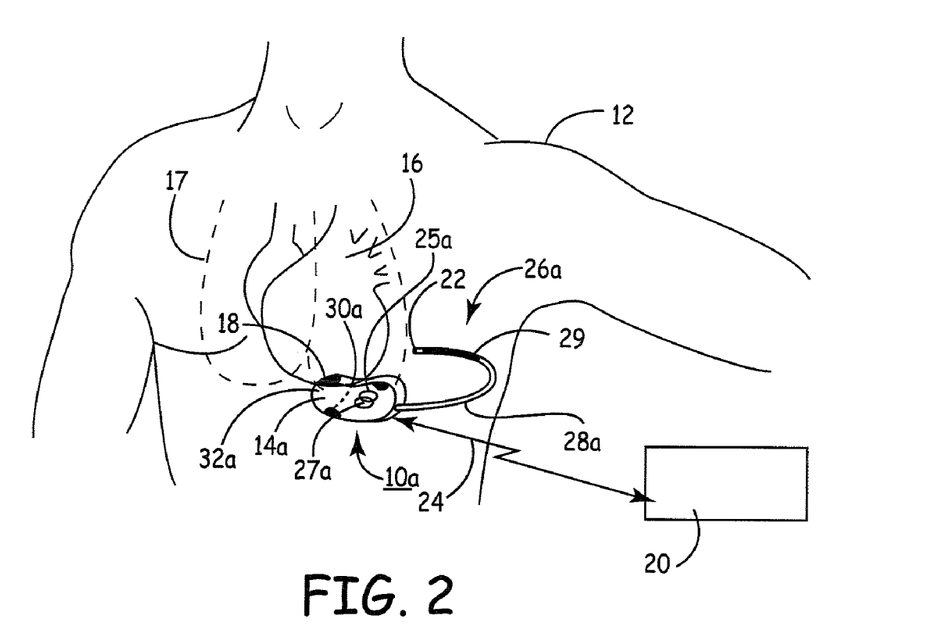
FIG. 2 shows an alternative embodiment of a SubQ ICD implanted in patient.

FIG. 2 is a schematic diagram of an alternative embodiment of a SubQ ICD 10a implanted in patient 12. A first acoustical sensor 25a is shown mounted within the housing of SubQ ICD 10a on the posterior-facing major surface 30. A second acoustical sensor 27a is shown on the anterior-facing major surface 32 of the housing 14a of SubQ ICD 10a. The first sensor 25a will be responsive to heart sounds and physiologic noise as described above. The second acoustical sensor 27a is shielded from the patient's heart by the housing 14a of SubQ ICD 10a and is therefore less responsive to heart sounds than the first sensor 25a. The second sensor 27a will generate a signal that includes physiologic and non-physiologic noise signals and can therefore be used in noise cancellation schemes for removing noise signals from the signal generated by the first sensor 25a.

In this embodiment, subcutaneous lead 28a is shown to include a distal sensing electrode 22 located at distal end 26 of lead 28a. Electrode 22 may be used in combination with any of the electrodes included in the sensing electrode array 18 formed on housing 14a for sensing subcutaneous ECG signals for use in detecting heart rhythms and timing electrical stimulation therapies.

Figure 3:
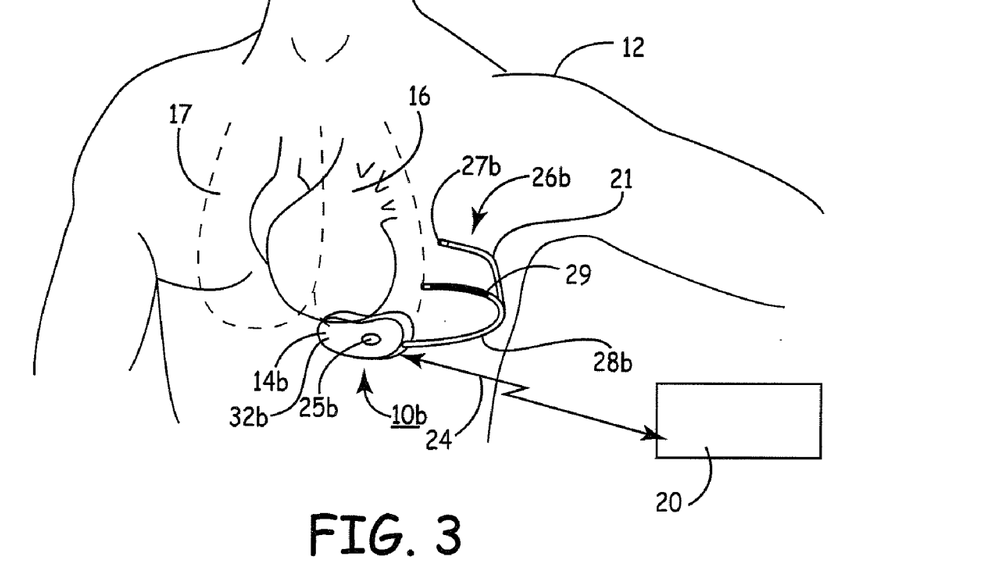
FIG. 3 shows another embodiment of a SubQ ICD implanted in patient.

FIG. 3 is a schematic diagram of another embodiment of a SubQ ICD 10b implanted in patient 12. A first acoustical sensor 25b is shown mounted on a superior major side 32 of housing 14b, on an internal surface of major side 32 within the housing 14b of SubQ ICD 10b. Subcutaneous lead 28b is shown as a bifurcated lead having a branch 21 extending posteriorly from SubQ ICD 10b. A second acoustical sensor 27b is shown carried by the branch 21 of subcutaneous lead 28b such that the lungs 17 are between the second sensor 27b and the patient's heart 16. The first sensor 25b generates a signal responsive to heart sounds, including any physiologic and non-physiologic noise sources as described above. The second sensor 27b is positioned such that the patient's lungs filter cardiac sounds from the signal generated by second sensor 27b. As such, the acoustical signal generated by second sensor 27b is less responsive to cardiac sounds than the signal generated by the first sensor 25b. The acoustical signal generated by the second sensor 27b, however, will be responsive to any physiologic and non-physiologic noise sources present such that the second acoustical signal can be used in noise cancellation schemes for removing non-cardiac signals from the acoustical signal generated by the first sensor 25b.

Figure 4:
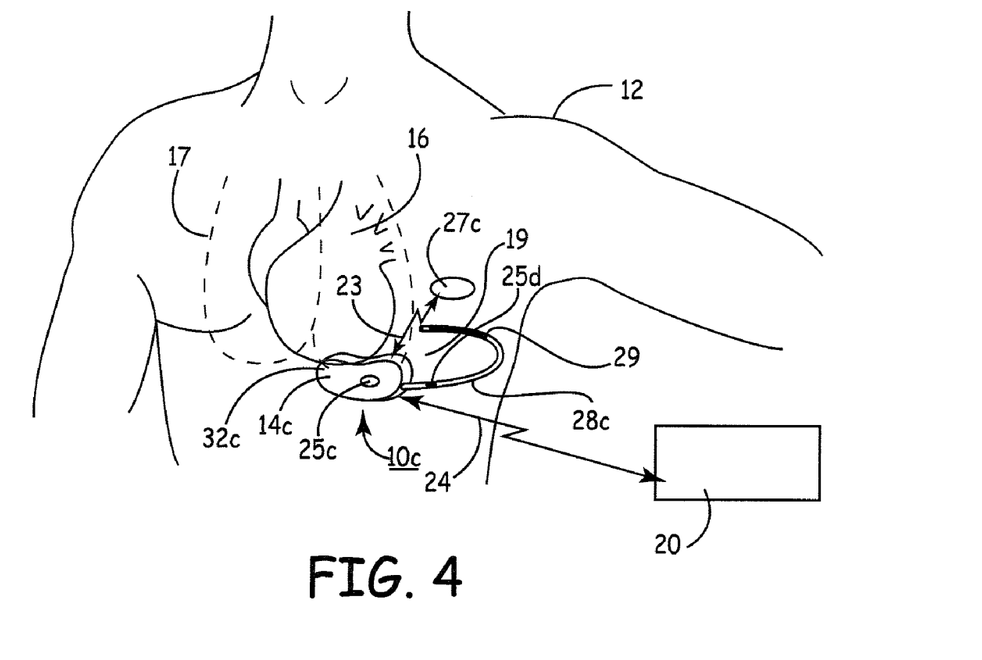
FIG. 4 shows yet another embodiment of a SubQ ICD implanted in patient.

FIG. 4 is a schematic diagram of yet another embodiment of a SubQ ICD 10c implanted in patient 12. A first sensor 25c is shown mounted on a superior major side 32c on an interior surface of side 32c within the housing 14c of SubQ ICD 10c. A second sensor 27c is shown implanted remotely from SubQ ICD 10c in the patient's back such that the lungs 17 are between the sensor 27c and the patient's heart 16. The first sensor 25c is responsive to heart sounds and any physiologic and non-physiologic noise sources as described above. The second sensor 27c is less responsive to the heart sounds and is used in noise cancellation schemes for removing non-cardiac signals from the acoustical signal generated by the first sensor 25c as described above.

The second sensor 27c is shown in telemetric communication with SubQ ICD 10c by communication link 23, which may be an RF link, for example, established via Bluetooth, WiFi, MICS, or as described in the above referenced Goedeke '432 patent. Acoustical signals generated by sensor 27c are transmitted to SubQ ICD 10c via link 23 for processing by SubQ ICD 10c in noise cancellation schemes for removing non-cardiac signals from the signal generated by first sensor 25c.

Lead 28c is shown to include acoustical sensor 25d located near proximal end 19 of lead 28c. Sensor 25d may be provided for generating a signal responsive to heart sounds as an alternative to housing-based sensor 25c. Sensor 25d will generate a signal that is more sensitive to cardiac signals than sensor 27c located opposite the lungs 17 from heart 16.

It is recognized that numerous variations may be conceived by one having skill in the art and the benefit of the teachings provided herein for positioning two or more acoustical sensors to provide at least one sensor that is more sensitive to cardiac signals than a second sensor. Such sensors may be remotely placed lead-based or leadless sensors, such as sensors 27b and 27c, respectively, or incorporated in or on an implantable medical device housing. Lead-based sensors may be implemented on transveous intracardiac leads or catheters as well as subcutaneous or epicardial leads. It is further recognized that acoustical sensors may be implemented in conjunction with any implantable medical device that relies on acoustical sensing of physiological signals and embodiments described herein are not limited to the illustrative embodiments shown in FIGS. 1 through 4 relating to a SubQ ICD. Other IMD systems which may include acoustical sensors include pacemakers, cardiac or other physiological monitoring devices, neurostimulators, drug pumps, or the like.

Figure 5:
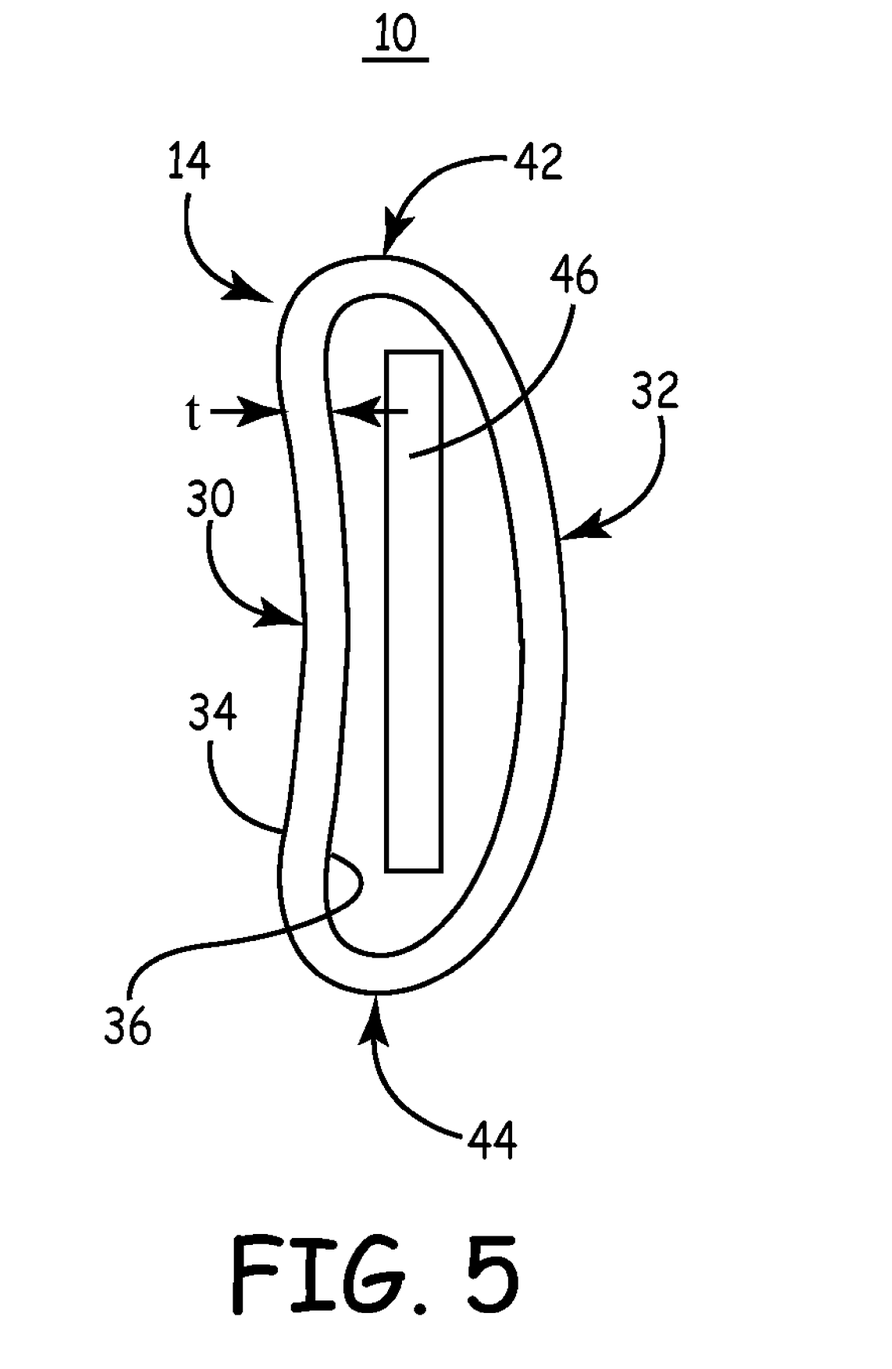
FIG. 5 is a sectional view of a SubQ ICD.

FIG. 5 is a sectional view of SubQ ICD 10. Housing 14 may be constructed of stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronics circuitry 46 enclosed in housing 14 may be incorporated on a flex circuit, printed circuit board (PCB) or ceramic substrate with integrated circuits packaged in leadless chip carriers and/or chip scale packaging (CSP) or chip-on-board packaging.

Housing 14 includes a first major side 30 and a second major side 32 separated by minor sides 42 and 44. When SubQ ICD 10 is implanted in an anterior location, the first major side 30 is adapted to be placed in a generally medial or posterior-facing position, e.g., toward the patient's heart. The second major side 32 is adapted to be facing outward toward the skin. As used herein, "inwardly-facing" refers to a side of the housing 14 that is the deep side of the implanted device, which may be generally posterior-, anterior-, or medially-facing depending on the implant site. As used herein, "outwardly-facing" refers to a side of the housing 14 that is facing outward toward the patient's skin after implantation. First major side 30 would be the "inwardly-facing" side and second major side 32 is the "outwardly-facing side" in the embodiment shown in FIG. 5.

Housing 14 has a thickness t separating an exterior surface 34 from interior surface 36. In various embodiments of the present invention, an acoustical sensor may be positioned anywhere along the interior surface 36 or the exterior surface 34 along any of the major or minor sides 30, 32 and 42, 44 and electrically coupled to circuitry 46. It is further recognized that an acoustical sensor may be configured to extend through the thickness t of housing 14.

Figure 6:
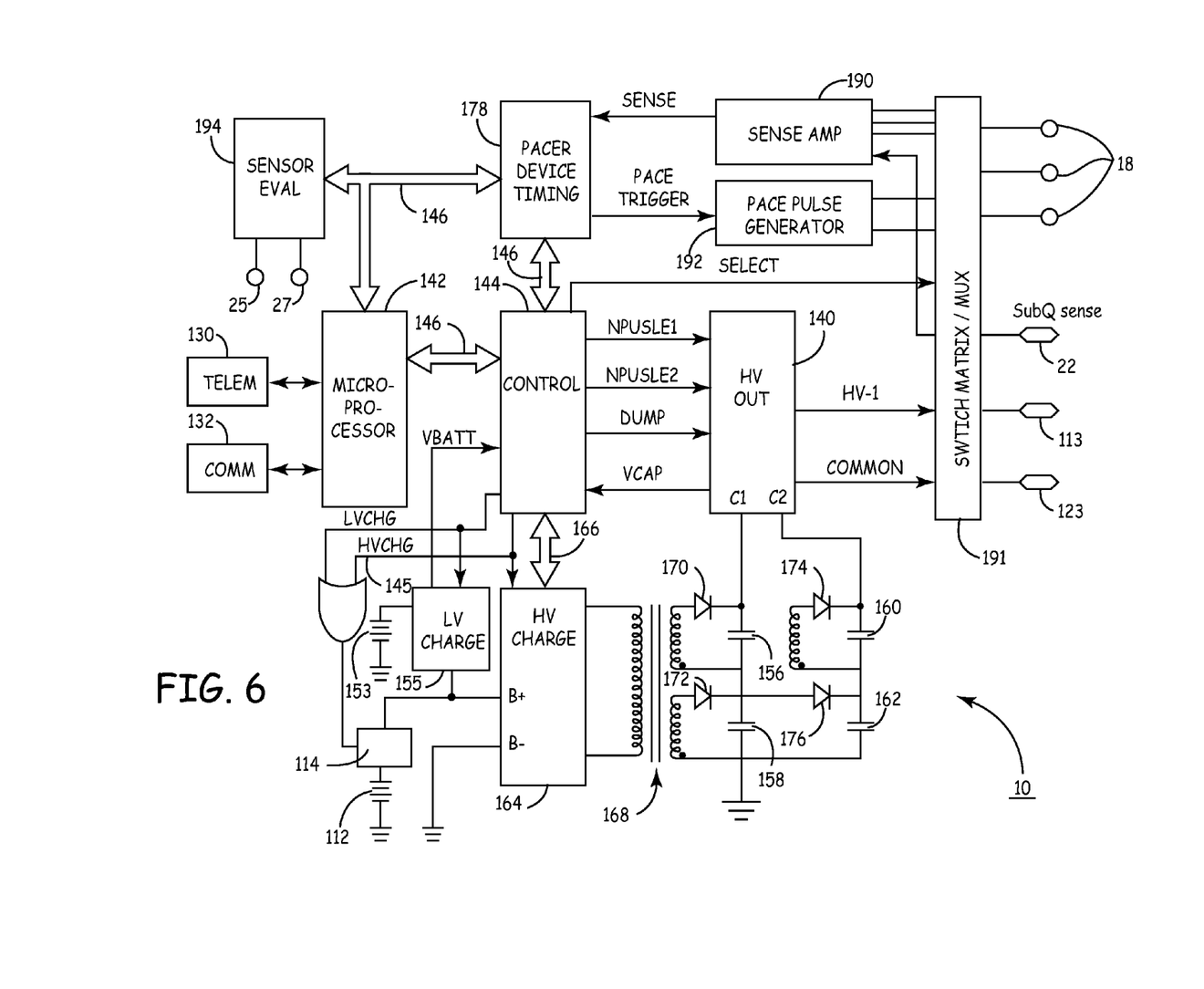
FIG. 6 is a functional block diagram of circuitry included in an IMD in which the present invention may be implemented, such as a SubQ ICD.

FIG. 6 is a functional block diagram of circuitry included in an IMD in which the present invention may be implemented, such as a SubQ ICD. SubQ ICD 10 functions are generally controlled by software, firmware and hardware that cooperatively operate to monitor ECG signals, determine when a cardioversion/defibrillation (CV/DF) shock or pacing is necessary, and deliver prescribed CV/DF and pacing therapies. The particular architecture of SubQ ICD 10 for controlling and executing device functions may include an application specific integrated circuit (ASIC), an electronic circuit, a processor (shared, dedicated, or group) and memory that execute one or more software or firmware programs, a combinational logic circuit, or other suitable components or combinations of components that provide the described functionality.

Such functionality includes delivering single phase, simultaneous biphasic, or sequential biphasic CV/DF shocks using the SubQ ICD housing 14 (shown in FIG. 5) coupled to the COMMON output 123 of high voltage output circuit 140 a CV/DF electrode 29 (shown in FIG. 1) coupled to the HV output terminal 113. Circuitry for delivering CV/DF shocks may generally correspond to circuitry set forth in commonly assigned U.S. Pat. No. 5,163,427 (Keimel) and U.S. Pat. No. 5,188,105 (Keimel).

In FIG. 6, sense amplifier 190 in conjunction with pacer/device timing circuit 178 processes the subcutaneous ECG sense signals received from sensing vectors selected from subcutaneous electrode array 18 and sensing electrode 22. The subcutaneous ECG signals are passed through the switch matrix/multiplexer 191 to the input of the sense amplifier 190 that, in conjunction with pacer/device timing circuit 178, evaluates the sensed ECG signals. Sensing subcutaneous ECG signals in the presence of noise may be aided by the use of appropriate denial and extensible accommodation periods as generally described in U.S. Pat. No. 6,236,882 (Lee, et al.).

Bradycardia or asystole is typically determined by expiration of an escape interval timer within the pacer timing circuit 178 and/or the control circuit 144. Pace trigger signals are applied to the pacing pulse generator 192 causing generation of pacing pulses when the escape interval expires (the interval between successive R-waves exceeds the escape interval). Bradycardia pacing may be temporarily provided to maintain cardiac output during recovery from a CV/DF shock. Low voltage power supply 153 provides power to circuitry included in SubQ ICD 10 and to low voltage charging circuitry 155 for generating low voltage pacing pulses. Pace pulse generator 192 may alternatively be incorporated in the HV output circuitry 140 for delivering pacing pulses of adequate energy for capturing the heart using subcutaneous electrodes.

Detection of a malignant tachyarrhythmia is determined in the control circuit 144 as a function of the intervals between R-wave sense event signals determined from one or more of the selected ECG signals. The R-wave sense event signals are output from the pacer/device timing 178 and sense amplifier circuit 190 to the control circuit 144. It should be noted that implemented arrhythmia detection algorithms may utilize not only interval based signal analysis methods but also supplemental sensors and morphology processing methods and apparatus. Certain steps in the performance of the rhythm detection algorithms are cooperatively performed in microprocessor 142, including associated RAM and ROM with stored detection criteria that may be programmed into RAM via a telemetry interface 130.

Bradycardia, asystole and arrhythmia detection algorithms may employ heart sound signals for detecting or confirming a heart rhythm in some embodiments. Acoustical sensor signals are received by sensor evaluation module 194 from first and second acoustical sensors 25 and 27. The sensor evaluation module 194 uses the acoustical signal from sensor 27 that is less responsive to heart sounds to correct the acoustical signal from sensor 25 that is more responsive to heart sounds but includes non-cardiac noise. In particular, sensor evaluation module 194 may subtract a weighted noise signal sensed by sensor 27 from the first acoustical signal sensed sensor 25 to remove non-cardiac noise from the first acoustical sensor signal. The sound common to both sensors is effectively cancelled, leaving the heart sound signals to be further evaluated for amplitude and timing. Alternatively, the sensor evaluation block 194 may use active filtering techniques such as multiple narrow band bandpass filters and/or fast Fourier transform methods to eliminate physiologic noise signals allowing the heart sounds signals to be evaluated. These techniques are described in U.S. Pat. No. 6,478,744 "Method of Using an Acoustic Coupling for Determining a Physiologic Signal" to Mohler and U.S. Publication 2005/0043763 "Processing Pulse Signal in Conjunction with ECG Signal to Detect Pulse in External Defibrillation" to Marcovecchio, et al, both incorporated herein by reference in their entireties.

Other sensor signals may be employed by SubQ ICD 10 and processed by sensor evaluation module 194, e.g. signals corresponding to respiration, patient activity, blood or tissue chemistry, blood temperature, or other mechanical signals. Such signals may be used in detecting heart rhythms or cardiac conditions for diagnostic purposes or controlling electrical stimulation therapies.

Data and commands are exchanged between microprocessor 142 and timing and control circuit 144, pacer/device timing circuit 178, and high voltage output circuit 140 via a bi-directional data/control bus 146. The pacer/device timing circuit 178 and the control circuit 144 are clocked at a slow clock rate. The microprocessor 142 is normally asleep, but is awakened and operated by a fast clock by interrupts developed by sensed cardiac event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

When a malignant tachycardia is detected, high voltage capacitors 156, 158, 160, and 162 are charged to a pre-programmed voltage level by a high-voltage charging circuit 164 with charging current from high voltage battery 112 connected through switch 114. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 typically correspond to flat, aluminum electrolytic or wet tantalum construction.

High voltage capacitors 156, 158, 160 and 162 are charged by high voltage charge circuit 164 and a high frequency, high-voltage transformer 168. Proper charging polarities are maintained by diodes 170, 172, 174 and 176 interconnecting the output windings of high-voltage transformer 168 and the capacitors 156, 158, 160, and 162. Timing and control circuit 144 terminates the high voltage charge command HVCHG when the VCAP signal matches the programmed capacitor output voltage, i.e., the CV/DF peak shock voltage. Control circuit 144 then develops first and second control signals NPULSE 1 and NPULSE 2, respectively, that are applied to the high voltage output circuit 140 for triggering the delivery of cardioverting or defibrillating shocks.

SubQ ICD 10 includes telemetry circuit 130 so that it is capable of being programmed by means of external programmer 20 (FIG. 1) via a bidirectional telemetry link 24 (FIG. 1). Uplink telemetry allows device status and diagnostic/event data to be sent to an external device 20 for review by the patient's physician. Downlink telemetry allows the external programmer via physician control to program device function and set operating parameters, e.g. arrhythmia detection and therapy delivery parameters, for a specific patient.

SubQ ICD 10 may further include a communications unit 132 for allowing wireless communication directly between SubQ ICD 10 and a remote acoustical sensor implanted in the patient's body. Acoustical signals received telemetrically from a remote sensor may be provided to sensor evaluation module 194 via bus 146 for evaluating heart sound signals or for correcting another acoustical signal to remove non-cardiac noise to enable reliable heart sound evaluation. Alternatively, telemetry interface 130 may be used to communicate with a remotely implanted acoustical sensor.

Figure 7:
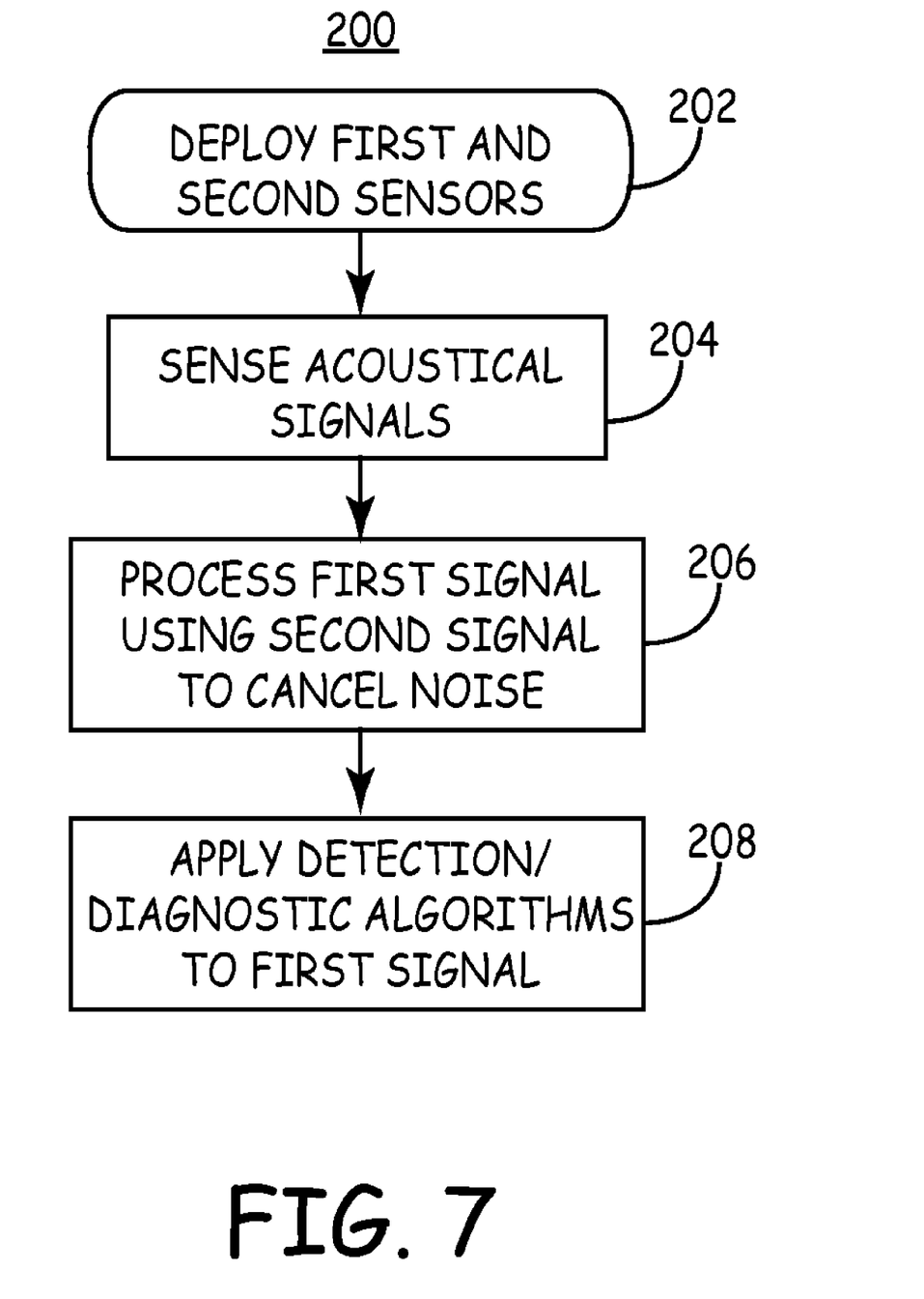
FIG. 7 is a flow chart of a method for detecting a cardiac condition using acoustical sensors.

FIG. 7 is a flow chart of a method 200 for detecting a cardiac condition using acoustical sensors. At block 202, first and second acoustical sensors are positioned at selected internal body locations such that the first sensor generates a signal that is more responsive to heart sounds than the signal generated by the second sensor. At block 204, acoustical signals are sensed simultaneously from the first and second acoustical sensors. Acoustical signals may be sensed continuously, periodically, or on a triggered basis depending on the particular monitoring or diagnostic algorithm employing the acoustical signals.

At block 206, the first signal is corrected by canceling non-cardiac noise present in the first signal using the second acoustical signal that includes the non-cardiac noise but is less responsive to heart sounds. Noise cancellation methods include straight subtraction, active noise control or adaptive noise cancellation methods. Methods that may be adapted for noise cancellation or suppression in heart sound signals are generally disclosed, for example, in U.S. Pat. No. 5,372,139 (Holls et al.), hereby incorporated herein by reference in its entirety. At block 208, the first signal is used by programmed detection, monitoring, or diagnostic algorithms for detecting or monitoring a cardiac condition. Such algorithms may include arrhythmia detection, hemodynamic monitoring, and capture monitoring. The corrected acoustical signal may be stored at block 208 in memory included in the implantable device for post-processing or later review by a clinician after transmitting the stored data to an external device.

Figure 8:
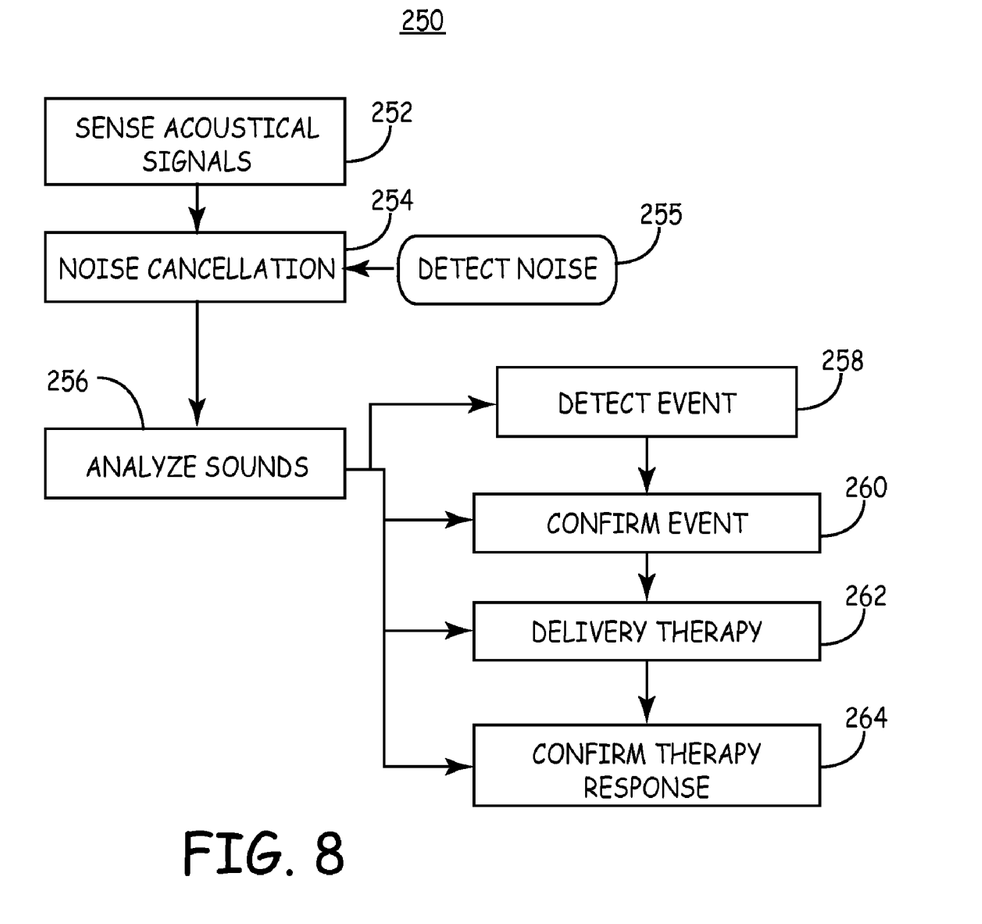
FIG. 8 is a flow chart of a method for using acoustical signals in monitoring a patient and/or in controlling a therapy delivery.

FIG. 8 is a flow chart of a method 250 for using acoustical signals in monitoring a patient and/or in controlling a therapy delivery. At block 252, acoustical signals are sensed from first and second acoustical sensors positioned in the body such that the first sensor is positioned to be responsive to a physiological sound of interest and the second sensor is positioned to be less responsive to the physiological sound of interest. At block 254, noise cancellation methods are applied to correct the first acoustical signal for noise using the second acoustical signal. At block 256, the physiological sounds of interest, for example heart sounds, are analyzed according to programmed algorithms for detecting particular sounds or signal characteristics.

The signal information obtained at block 256 from analyzing the corrected acoustical signal may be used at multiple levels of monitoring and therapy control functions. At block 258, the heart sound or other physiological sound information of interest is used by event detection algorithms. For example, heart sounds may be used in detecting arrhythmias including bradycardia, asystole, and tachycardia. Hemodynamic events may also be detected using heart sound information.

At block 260, an event detected using other sensor signals may be confirmed using the analyzed acoustical signal. For example, an arrhythmia may be detected initially using ECG interval analysis and then trigger heart sound analysis for confirming the presence of a detected arrhythmia.

At block 262, a therapy may be delivered in response to detected events. In some embodiments, the corrected acoustical signal information may be used in controlling the timing or duration of a delivered therapy, which may be an electrical stimulation therapy or a drug therapy. For example, heart sound information could be used to control the timing of electrical stimulation pulses delivered to the heart.

At block 264, the corrected acoustical signal may be used in verifying the effectiveness of a delivered therapy by measuring a response during or after therapy delivery. For example, heart sounds may be used in verifying capture of a stimulation pulse or verifying termination of a cardiac arrhythmia.

Acoustical sensors may be enabled to continuously monitor heart sounds on a beat-by-beat basis or on a triggered basis in response to an event detected using other physiological sensors, a therapy delivery, or other triggering event. Furthermore it is contemplated that noise cancellation methods for correcting the acoustical signal performed at block 254 are always performed whenever acoustical signals are sensed from the first signal. Alternatively, noise cancellation methods may be employed when the first acoustical signal is determined to be or expected to be noisy as indicated at block 255. Detection of noise in the first acoustical signal may trigger the second acoustical sensor operation and the execution of noise cancellation methods. Noise detection may be based on the frequency content, amplitude content, detected event rate or other noise detection schemes.

Alternatively, the second acoustical signal may be monitored to detect the presence of non-cardiac signals that would potentially interfere with the reliable detection of heart sounds. When the second acoustical signal is determined to have significant noise content at block 255, the noise cancellation methods are executed at block 254. In other embodiments, noise detection at block 255 may be based on anticipated noise presence, for example based on an activity sensor. An increase in patient activity may trigger operation of the second acoustical sensor and execution of noise cancellation methods at block 254.

It will be apparent from the foregoing that while particular embodiments of the invention have been illustrated and described, various modifications can be made without departing from the spirit and scope of the invention. Accordingly, it is not intended that the invention be limited, except as by the appended claims.

The invention claimed is:

1. An implantable medical device system, comprising:
a first acoustical sensor adapted to be operatively positioned in a first internal body location to have a first level of responsiveness for sensing heart sounds in a patient, and to generate a first signal responsive to the sensed heart sounds;
a second acoustical sensor adapted to be operatively positioned in a second internal body location to have a second level of responsiveness for sensing heart sounds in the patient less than the first level of responsiveness, and to generate a second signal responsive to the heart sounds; and
an implantable medical device comprising a housing and a processor enclosed in the housing, the processor configured to receive the first signal and the second signal and generate a corrected first signal by canceling non-cardiac signals in the first signal using the second signal;
wherein the housing comprises:
a first side, said first acoustical sensor being positioned on said first side; and
a second side opposite said first side, said second acoustical sensor being positioned on said second side.

2. The system of claim 1 wherein the
first side has an internal surface and an external surface, and
wherein the second side has an internal surface and an external surface, wherein at least one of the first acoustical sensor and the second acoustical sensor are positioned on the external surface of one of the first side and the second side of the housing.

3. The system of claim 2 wherein the first acoustical sensor is positioned along one of the internal surface and the external surface of the first side.

4. The system of claim 3 wherein the second acoustical sensor is positioned along one of the internal surface and the external surface of the second side.

5. The system of claim 1 wherein the implantable medical device comprises a telemetry circuit, and at least one of the first acoustical sensor and the second acoustical sensor comprises a telemetry circuit configured for bidirectional communication with the implantable medical device telemetry circuit.

6. A method for use in an implantable medical device system comprising an implantable medical device having a housing with a first side and a second side opposite the first side, comprising:

sensing heart sounds in a patient using a first acoustical sensor positioned on the first side of the housing to have a first level of responsiveness for sensing heart sounds in a patient, and to generate a first signal responsive to the sensed heart sounds;

sensing sounds in the patient using a second acoustical sensor positioned on the second side of the housing to have a second level of responsiveness for sensing heart sounds in the patient less than the first level of responsiveness, and to generate a second signal responsive to the heart sounds; and processing the first and second signals to generate a corrected first signal by canceling non-cardiac signals in the first signal using the second signal.

7. The method of claim 6 wherein the processing is performed in response to detecting noise.

8. The method of claim 7 wherein detecting noise comprises detecting noise content of one of the first signal and the second signal.

9. The method of claim 7 wherein detecting noise comprises detecting patient activity.

* * * * *